(12) United States Patent
Eisenschmid et al.

(10) Patent No.: US 8,664,451 B2
(45) Date of Patent: Mar. 4, 2014

(54) CONTROLLING THE NORMAL:ISO ALDEHYDE RATIO IN A MIXED LIGAND HYDROFORMYLATION PROCESS BY CONTROLLING THE OLEFIN PARTIAL PRESSURE

(75) Inventors: Thomas C. Eisenschmid, Cross Lanes, WV (US); Glenn A. Miller, South Charleston, WV (US); Jeffrey S. Sawrey, Westford, MA (US); Michael A. Brammer, Lake Jackson, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 13/517,419

(22) PCT Filed: Dec. 15, 2010

(86) PCT No.: PCT/US2010/060523
§ 371 (c)(1),
(2), (4) Date: Jun. 20, 2012

(87) PCT Pub. No.: WO2011/087696
PCT Pub. Date: Jul. 21, 2011

(65) Prior Publication Data
US 2012/0253080 A1    Oct. 4, 2012

(51) Int. Cl.
*C07C 45/50* (2006.01)

(52) U.S. Cl.
USPC ........................................................ 568/454

(58) Field of Classification Search
USPC ........................................................ 568/454
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,169,861 A | 10/1979 | Hughes |
| 4,247,486 A | 1/1981 | Brewester et al. |
| 4,567,302 A | 1/1986 | Sivaramakrishnan |
| 4,567,306 A | 1/1986 | Dennis et al. |
| 4,599,206 A | 7/1986 | Billig et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,873,213 A | 10/1989 | Puckette et al. |
| 4,885,401 A | 12/1989 | Billig et al. |
| 5,059,710 A | 10/1991 | Abatjoglou et al. |
| 5,102,505 A | 4/1992 | Sorensen |
| 5,110,990 A | 5/1992 | Blessing et al. |
| 5,113,022 A | 5/1992 | Abatjoglou et al. |
| 5,114,473 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,312,996 A | 5/1994 | Packett |
| 5,364,950 A | 11/1994 | Babin et al. |
| 5,449,653 A | 9/1995 | Briggs et al. |
| 5,741,945 A | 4/1998 | Bryant et al. |
| 5,763,671 A | 6/1998 | Bryant et al. |
| 5,874,640 A | 2/1999 | Bryant et al. |
| 5,892,119 A | 4/1999 | Bryant et al. |
| 6,090,987 A | 7/2000 | Billig et al. |
| 6,153,800 A | 11/2000 | Gelling et al. |
| 6,294,700 B1 | 9/2001 | Kanel et al. |
| 7,615,645 B2 | 11/2009 | Volland et al. |
| 2007/0093680 A1 | 4/2007 | Jeon et al. |
| 2007/0123735 A1 | 5/2007 | Jeon et al. |

FOREIGN PATENT DOCUMENTS

| | | |
|---|---|---|
| CN | 101293818 | 10/2008 |
| CN | 101565353 | 10/2009 |
| EP | 0590613 | 4/1994 |
| EP | 0874797 | 6/1997 |
| WO | 2006020287 | 2/2006 |
| WO | 2008088495 | 7/2008 |
| WO | 2008115740 | 9/2008 |

OTHER PUBLICATIONS

International Search Report for PCT App. No. PCT/US2010/060523 mailed Apr. 19, 2011.
Interantional Search Report for PCT App. No. PCT/US2010/060471 mailed Mar. 21, 2011.
International Search Report for PCT App. No. PCT/US2010/060480 mailed Apr. 7, 2011.

*Primary Examiner* — Sikarl Witherspoon
(74) *Attorney, Agent, or Firm* — Whyte Hirschboeck Dudek S.C.

(57) ABSTRACT

Control of an in-series, multiple, e.g., two, reaction zone, hydroformylation process for producing normal (N) and iso (I) aldehydes at a N:I ratio, the process comprising contacting an olefinically unsaturated compound, e.g., propylene, with carbon monoxide, hydrogen and a catalyst comprising (A) a transition metal, e.g., rhodium, (B) an organobisphosphite, and (C) an organomonophosphite ligand, the contacting conducted in first and subsequent reaction zones and at hydroformylation conditions comprising an olefinically unsaturated compound partial pressure in each zone, the control exercised by decreasing the olefinically unsaturated compound partial pressure in the first reaction zone to decrease the N:I ratio or increasing the olefinically unsaturated compound partial pressure in the first reaction zone to increase the N:I ratio.

18 Claims, No Drawings

CONTROLLING THE NORMAL:ISO ALDEHYDE RATIO IN A MIXED LIGAND HYDROFORMYLATION PROCESS BY CONTROLLING THE OLEFIN PARTIAL PRESSURE

FIELD OF THE INVENTION

This invention relates to hydroformylation processes. In one aspect, the invention relates to controlling the straight chain to branched isomer ratio of a hydroformylation process which uses a transition, e.g., rhodium, catalyst while in another aspect, the invention relates to such a process in which the metal is solubilized using a mixture of two phosphite ligands. In yet another aspect, the invention is controlling the straight chain to branched isomer ratio of the aldehyde product without destruction of the ligands.

BACKGROUND OF THE INVENTION

The variable normal (i.e., straight chain) to iso (i.e., branched) index (VNI) hydroformylation process uses a mixture of two phosphite ligands to allow for an adjustable selectivity in the normal:iso aldehyde product mixture. In particular the three component catalyst system uses a transition metal, typically rhodium (Rh), an organopolyphosphite ligand, typically an organobisphosphite ligand (obpl), and an organomonophosphite ligand (ompl) in which the organomonophosphite ligand to rhodium (ompl:Rh) molar ratio is typically maintained in excess of five to 1 (>5:1) and the organobisphosphite ligand to rhodium (obpl:Rh) molar ratio is controlled between 0 and 1:1 to control the N:I over the range which would be obtained based solely on an ompl:Rh molar ratio (typically between 1 and 5) to that obtained for an obpl:Rh molar ratio (typically between 20 and 40 for propylene). The conventional method of controlling N:I is to control the organobisphosphite ligand to rhodium ratio. In particular the method for lowering N:I is to lower the concentration of the organobisphosphite ligand through the natural decomposition of the ligand through oxidation and hydrolysis. The difficulty with this method, however, is that it is slow, i.e., it takes time for the natural decomposition of the organobisphosphite ligand. Increasing the rate of decomposition of the organobisphosphite ligand is known, but this method increases the expense of the process. Of interest is a method for controlling N:I without decomposing the expensive organobisphosphite ligand.

BRIEF SUMMARY OF THE INVENTION

In one embodiment the invention is a method of controlling a multiple reaction zone, hydroformylation process (such as that described in WO 2008/115740 A1) for producing normal (N) and iso (I) aldehydes at a N:I ratio, the process comprising contacting an olefinically unsaturated compound with carbon monoxide, hydrogen and a catalyst comprising (A) a transition metal, preferably rhodium, (B) an organopolyphosphite, preferably an organobisphosphite, ligand, and (C) an organomonophosphite ligand, the contacting conducted in first and subsequent reaction zones and at hydroformylation conditions comprising an olefinically unsaturated compound partial pressure (olefin partial pressure) in each zone, the method comprising decreasing the olefin partial pressure in the first reaction zone to decrease the N:I ratio or increasing the olefin partial pressure in the first reaction zone to increase the N:I ratio.

In one embodiment the invention is a method of controlling a multiple-reaction zone, hydroformylation process for producing normal (N) and iso (I) aldehydes at a N:I ratio, the process comprising contacting an olefinically unsaturated compound with carbon monoxide, hydrogen and a catalyst comprising (A) a transition metal, (B) an organobisphosphite, and (C) an organomonophosphite ligand, the contacting conducted in first and subsequent reaction zones and at hydroformylation conditions comprising an olefinically unsaturated compound partial pressure in each zone, the method comprising changing the N:I ratio by one or more of the following:

(1) Changing the temperature in the first reaction zone;
(2) Feeding up to 20% of the total olefin feed into a subsequent reaction zone;
(3) Reducing the amount of olefin feed into a subsequent reaction zone; and
(4) Changing the olefin feed rate to the first reaction zone.

DETAILED DESCRIPTION OF THE PREFERRED EMBODIMENT

All references to the Periodic Table of the Elements refer to the Periodic Table of the Elements published and copyrighted by CRC Press, Inc., 2003. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, definitions (to the extent not inconsistent with any definitions specifically provided in this disclosure), and general knowledge in the art.

All percentages, preferred amounts or measurements, ranges and endpoints are inclusive, that is, "up to 10" includes 10. "At least" is equivalent to "greater than or equal to," and "at most" is, thus, equivalent "to less than or equal to." Numbers are approximate unless otherwise specifically noted. All ranges from a parameter described as "at least," "greater than," "greater than or equal to" or similarly, to a parameter described as "at most," "up to," "less than," "less than or equal to" or similarly are preferred ranges regardless of the relative degree of preference indicated for each parameter. Thus a range that has an advantageous lower limit combined with a most preferred upper limit is preferred for the practice of this invention. The term "advantageous" is used to denote a degree of preference more than required, but less than is denoted by the term "preferably." Numerical ranges are provided within this disclosure for, among other things, the relative amount of reagents and process conditions.

The hydroformylation process, its reagents, conditions and equipment, are well known and described in, among other references, U.S. Pat. No. 4,169,861, 5,741,945, 6,153,800 and 7,615,645, EP 0 590 613 A2 and WO 2008/115740 A1. Typically, an olefinically unsaturated compound, e.g., propylene, is fed with synthesis gas, i.e., carbon monoxide (CO) and hydrogen ($H_2$), along with a three-component catalyst comprising a transition metal, preferably rhodium, and an organopolyphosphite, preferably an organobisphosphite, and an organomonophosphite ligand, the contacting conducted at hydroformylation conditions into a multi-reactor system coupled in series, i.e., the output of the first reaction zone is fed as input to the subsequent reaction zone. The processing techniques can correspond to any of the known processing techniques employed in conventional hydroformylation processes. For instance, the processes can be conducted in either the liquid or gaseous states and in a continuous, semi-continuous or batch fashion and involve a liquid recycle and/or gas recycle operation or a combination of such systems as desired. Likewise, the manner or order of addition of the reaction ingredients, catalyst and solvent are also not critical and may be accomplished in any conventional fashion.

Olefinically-unsaturated compounds suitably employed in the process of this invention are those that are capable of participating in a hydroformylation process to produce corresponding aldehyde product(s) and capable of being separated from the crude liquid hydroformylation product stream via vaporization. For the purposes of this invention, an "olefin" is defined as an aliphatic organic compound containing at least carbon and hydrogen atoms and having at least one carbon-carbon double bond (C=C). Preferably, the olefin contains one or two carbon-carbon double bonds, more preferably, one carbon-carbon double bond. The double bond(s) can be located at a terminal position along the carbon chain (alpha olefin) or at any internal position along the chain (internal olefin). Optionally, the olefin can comprise elements other than carbon and hydrogen including, for example, nitrogen, oxygen, and halogens, preferably, chlorine and bromine. The olefin can also be substituted with functional substituents including, for example, hydroxy, alkoxy, alkyl and cycloalkyl substituents. Preferably, the olefin used in the process of this invention comprises a substituted or unsubstituted olefin having a total of from 3 to 10 carbon atoms. Illustrative olefins suitable for the process of this invention include, without limitation, isomers of the following mono-olefins of butene, pentene, hexene, heptene, octene, nonene and decene, with specific non-limiting examples including 1-butene, 2-butene, 1-pentene, 2-pentene, and 1-hexene, 2-hexene, 3-hexene, and similarly, for heptene, octene, nonene, and decene. Other non-limiting examples of suitable olefins include 2-methyl propene (isobutylene), 2-methylbutene, cyclohexene, butadiene, isoprene, 2-ethyl-1-hexene, styrene, 4-methyl styrene, 4-isopropyl styrene, 4-tert-butyl styrene, alpha-methyl styrene, 3-phenyl-1-propene, 1,4-hexadiene, 1,7-octadiene; as well as alkenols, for example, pentenols; alkenals, for example, pentenals; such species to include allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, 3-butenenitrile, 5-hexenamide, and dicyclopentadiene. The olefin can also be a mixture of olefins of similar or different molecular weights or structures (optionally with inerts such as the corresponding saturated alkanes).

Preferably, the olefin stream used in the process of this invention comprises a C4 raffinate I or C4 raffinate II isomeric mixture comprising butene-1, butene-2, isobutylene, butane, and optionally, butadiene. The C4 raffinate I stream comprises from 15 to 50 percent isobutylene and from 40 to 85 percent normal butenes, by weight, any remainder to 100 percent comprising primarily n-butane and isobutane. The normal butenes are generally a mixture of butene-1 and butene-2 (cis- and trans-forms). The relative proportions stream components depend upon the composition of the petroleum feed, the conditions employed in steam cracking or catalytic cracking operation, and in the subsequent process steps, from which the C4 stream is derived. The C4 raffinate II stream comprises from about 15 to 55 percent 1-butene, from about 5 to about 15 percent 2-butene (5 to 35 percent trans-2-butene), from about 0.5 to about 5 percent isobutylene, and from about 1 to about 40 percent butane, by volume. More preferably the olefin stream comprises propylene or mixtures of propylene and propane and other inerts.

Hydrogen and carbon monoxide are also required for the hydroformylation step of this invention. These gases can be obtained from any available source including petroleum cracking and refinery operations. Synthesis gas mixtures are preferably employed. The $H_2$:CO molar ratio of gaseous hydrogen to carbon monoxide can range, preferably, from about 1:10 to about 100:1, the more preferred $H_2$:CO molar ratio being from about 1:10 to about 10:1, and even more preferably, from about 2:1 to about 1:2. The gases are generally quantified by their partial pressures in the reactor based on their mole fraction in the gas phase (as measured by gas chromatography) and the total pressure using Dalton's Law. As used in the context of this invention, "syngas partial pressure" is the sum of the partial pressure of CO and the partial pressure of $H_2$.

Suitable metals that make up the transition metal-ligand complex catalyst include Group VIII metals selected from rhodium (Rh), cobalt (Co), iridium (Ir), ruthenium (Ru), iron (Fe), nickel (Ni), palladium (Pd), platinum (Pt), osmium (Os) and mixtures of two or more of these metals, with the preferred metals being rhodium, cobalt, iridium and ruthenium, more preferably rhodium, cobalt and ruthenium, and most preferably, rhodium. Other permissible metals include Group VIB metals selected from chromium (Cr), molybdenum (Mo), tungsten (W), and mixtures of two or more of these metals. Mixtures of metals from Groups VIB and VIII may also be used in this invention.

"Complex" and like terms means a coordination compound formed by the union of one or more electronically rich molecules or atoms (i.e., ligand) with one or more electronically poor molecules or atoms (e.g., transition metal). For example, the organomonophosphite ligand used in the practice of this invention possesses one phosphorus (III) donor atom having one unshared pair of electrons, which is capable of forming a coordinate covalent bond with the metal. The organopolyphosphite ligand used in the practice of this invention possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the transition metal. The ultimate composition of the complex catalyst may also contain an additional ligand, for example, hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R)_2PO$ and $RP(O)(OH)O$ (in which each R is the same or different and is a substituted or unsubstituted hydrocarbon radical, for example, alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_2H_5CN$, $CH_3CN$, $NH_3$, pyridine, $(C_2H_5)_3N$, mono-olefin, diolefin and triolefin, tetrahydrofuran, and the like.

The number of available coordination sites on the transition metal is well known in the art and depends upon the particular transition metal selected. The catalytic species may comprise a complex catalyst mixture in their monomeric, dimeric or higher nuclearity forms, which preferably are characterized by at least one organophosphorus-containing molecule complexed per one molecule of metal, for example, rhodium. For instance, the catalytic species of the preferred catalyst employed in the hydroformylation reaction may be complexed with carbon monoxide and hydrogen in addition to either the organopolyphosphite ligand or the organomonophosphite ligand.

The organopolyphosphite ligand broadly comprises a plurality of phosphite groups, each of which contains one trivalent phosphorus atom bonded to three hydrocarbyloxy radicals. Hydrocarbyloxy radicals that link and bridge two phosphite groups are more properly referred to as "divalent hydrocarbyldioxy radicals." These bridging di-radicals are not limited to any particular hydrocarbyl species. On the other hand, hydrocarbyloxy radicals that are pendant from a phosphorus atom and not bridging two phosphite groups (i.e., terminal, non-bridging), are each required to consist essentially of an aryloxy radical. "Aryloxy" broadly refers to either of two types of aryloxy radicals: (1) a monovalent aryl radical bonded to a single ether linkage, as in —O-aryl, wherein the aryl group comprises a single aromatic ring or multiple aromatic rings that are fused together, directly linked, or indirectly linked (such that different aromatic groups are bound to a common group such as a methylene or ethylene moiety), or (2) a divalent arylene radical bonded to two ether linkages, as in —O-arylene-O— or —O-arylene-arylene-O—, in which the arylene group comprises a divalent hydrocarbon radical having a single aromatic ring or multiple aromatic rings that are fused together, directly linked, or indirectly linked (such that the different aromatic groups are bound to a common group such as a methylene or ethylene moiety). Preferred aryloxy groups contain one aromatic ring or from 2 to 4 fused or linked aromatic rings, having from about 5 to about 20 carbon atoms, for example, phenoxy, naphthyloxy, or biphenoxy, as well as arylenedioxy radicals, such as, phenylenedioxy, naphthylenedioxy, and biphenylenedioxy. Any of these radicals and groups may be unsubstituted or substituted.

Preferred organopolyphosphite ligands comprise two, three or higher numbers of phosphite groups. Mixtures of such ligands may be employed if desired. Achiral organopolyphosphites are preferred. Representative organopolyphosphites include those of formula (I):

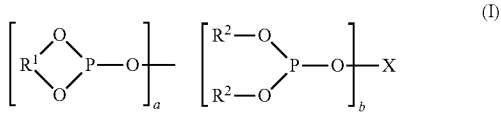
(I)

in which X represents a substituted or unsubstituted n-valent organic bridging radical containing from 2 to 40 carbon atoms, each $R^1$ is the same or different and represents a divalent arylene radical containing from 6 to 40 carbon atoms, preferably, from 6 to 20 carbon atoms; each $R^2$ is the same or different and represents a substituted or unsubstituted monovalent aryl radical containing from 6 to 24 carbon atoms; a and b can be the same or different and each has a value of 0 to 6, with the proviso that the sum of a+b is 2 to 6 and n equals a+b. When a has a value of 2 or more, each $R^1$ radical may be the same or different, and when b has a value of 1 or more, each $R^2$ radical may be the same or different.

Representative n-valent (preferably divalent) hydrocarbon bridging radicals represented by X include both acyclic radicals and aromatic radicals, such as alkylene, alkylene-Qm-alkylene, cycloalkylene, arylene, bisarylene, arylene-alkylene, and arylene-$(CH_2)_y$-Q-$(CH_2)_y$-arylene radicals, wherein each y is the same or different and is a value of 0 or 1. Q represents a divalent bridging group selected from —$C(R^3)_2$—, —O—, —S—, —$NR^4$—, —$Si(R^5)_2$— and —CO—, wherein each $R^3$ is the same or different and represents hydrogen, an alkyl radical having from 1 to 12 carbon atoms, phenyl, tolyl, and anisyl, $R^4$ represents hydrogen or a substituted or unsubstituted monovalent hydrocarbon radical, for example, an alkyl radical having 1 to 4 carbon atoms; each $R^5$ is the same or different and represents hydrogen or an alkyl radical, preferably, a $C_{1-10}$ alkyl radical, and m is a value of 0 or 1. The more preferred acyclic radicals represented by X above are divalent alkylene radicals while the more preferred aromatic radicals represented by X are divalent arylene and bisarylene radicals, such as disclosed more fully, for example, in U.S. Pat. Nos. 4,769,498; 4,774,361; 4,885,401; 5,179,055; 5,113,022; 5,202,297; 5,235,113; 5,264,616; 5.364,950; 5,874,640; 5,892,119; 6,090,987; and 6,294,700.

Illustrative preferred organopolyphosphites include bisphosphites such as those of formulae (II) to (IV):

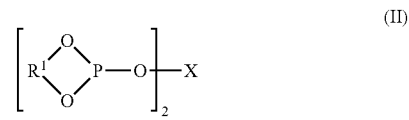
(II)

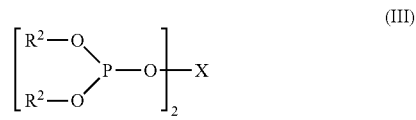
(III)

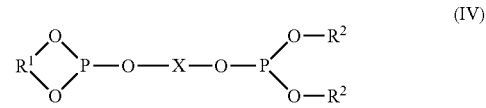
(IV)

in which $R^1$, $R^2$ and X of formulae (II) to (IV) are the same as defined above for formula (I). Preferably X represents a divalent hydrocarbon radical selected from alkylene, arylene, arylene-alkylene-arylene, and bisarylene; $R^1$ represents a divalent hydrocarbon radical selected from arylene, arylene-alkylene-arylene, and bisarylene; and each $R^2$ radical represents a monovalent aryl radical. Organopolyphosphite ligands of such formulae (II) to (IV) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996 and 5,364,950.

Representative of more preferred classes of organobisphosphites are those of the formulae (V) to (VII).

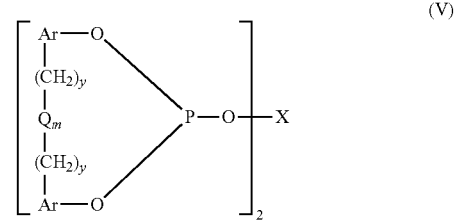
(V)

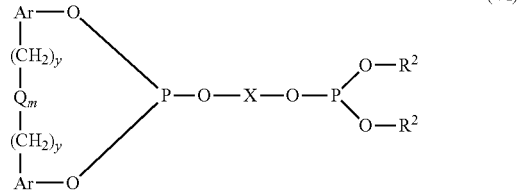
(VI)

-continued

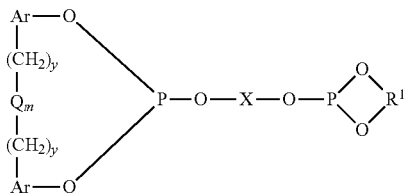
(VII)

in which Q, $R^1$, $R^2$, X, m, and y are as defined above, and each Ar is the same or different and represents a substituted or unsubstituted divalent aryl radical. Most preferably, X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —C$(R^3)_2$ where each $R^3$ is the same or different and represents hydrogen or a $C_{1-10}$ alkyl radical, preferably, methyl. More preferably, each aryl radical of the above-defined AR, X, $R^1$ and $R^2$ groups of formulae (V) to (VII) may contain 6 to 18 carbon atoms and the radicals may be the same or different, while the preferred alkylene radicals of X may contain 2 to 18 carbon atoms. In addition, preferably the divalent Ar radicals and divalent aryl radicals of X of the above formulae are phenylene radicals in which the bridging group represented by —$(CH_2)_y$-$(Q)_m$-$(CH_2)_y$— is bonded to the phenylene radicals in positions that are ortho to the oxygen atoms of the formulae that connect the phenylene radicals to their phosphorus atom. Any substituent radical when present on such phenylene radicals is preferably bonded in the para and/or ortho position of the phenylene radicals in relation to the oxygen atom that bonds the given substituted phenylene radical to its phosphorus atom.

Moreover, if desired any given organopolyphosphite in the above formulae (I) to (VII) may be an ionic phosphite, that is, may contain one or more ionic moieties selected from the group consisting of: —$SO_3M$, wherein M represents an inorganic or organic cation, —$PO_3M$ wherein M represents an inorganic or organic cation, —$N(R^6)3X^1$, wherein each $R^6$ is the same or different and represents a hydrocarbon radical containing from 1 to 30 carbon atoms, for example, alkyl, aryl, alkaryl, aralkyl, and cycloalkyl radicals, and $X^1$ represents inorganic or organic anion, —$CO_2M$ wherein M represents inorganic or organic cation, as described, for example, in U.S. Pat. Nos. 5,059,710; 5,113,022; 5,114,473 and 5,449,653. Thus, if desired, such organopolyphosphite ligands may contain from 1 to 3 such ionic moieties; however, preferably only one such ionic moiety is substituted on any given aryl moiety when the organopolyphosphite ligand contains more than one such ionic moiety. Suitable cationic species of M include, without limitation, hydrogen (i.e., a proton), the cations of the alkali and alkaline earth metals, for example, lithium, sodium, potassium, cesium, rubidium, calcium, barium, magnesium and strontium, the ammonium cation and quaternary ammonium cations, phosphonium cations, arsonium cations and iminium cations. Suitable anions $X^1$ include, for example, sulfate, carbonate, phosphate, chloride, acetate, oxalate and the like.

Of course any of the $R^1$, $R^2$, X, Q and Ar radicals of such non-ionic and ionic organopolyphosphites of formulae (I) to (VII) above may be substituted if desired, with any suitable substituent, optionally containing from 1 to 30 carbon atoms, that does not adversely affect the desired result of the process of this invention. Substituents that may be on the radicals in addition, of course, to corresponding hydrocarbon radicals such as alkyl, aryl, aralkyl, alkaryl and cyclohexyl substituents, may include for example silyl radicals such as —$Si(R^7)_3$; amino radicals such as —$N(R^7)_2$; phosphine radicals such as -aryl-$P(R^7)_2$; acyl radicals such as —$C(O)R^7$; acyloxy radicals such as —$OC(O)R^7$; amido radicals such as —$CON(R^7)_2$ and —$N(R^7)COR^7$; sulfonyl radicals such as —$SO_2R^7$, alkoxy radicals such as —$OR^7$; sulfinyl radicals such as —$SOR^7$; sulfenyl radicals such as —$SR^7$; phosphonyl radicals such as —$P(O)(R^7)_2$; as well as halogen, nitro, cyano, trifluoromethyl, hydroxy radicals, and the like, wherein preferably each $R^7$ radical individually represents the same or different monovalent hydrocarbon radical having from 1 to about 18 carbon atoms (for example, alkyl, aryl, aralkyl, alkaryl and cyclohexyl radicals) with the proviso that in amino substituents such as —$N(R^7)_2$ each $R^7$ taken together can also represent a divalent bridging group that forms a heterocyclic radical with the nitrogen atom, and in amido substituents such as —$C(O)N(R^7)_2$ and —$N(R^7)COR^7$ each $R^7$ bonded to N can also be hydrogen. Of course any of the substituted or unsubstituted hydrocarbon radicals groups that make up a particular given organopolyphosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl and naphthyl; aralkyl radicals such as benzyl, phenylethyl, and triphenylmethyl; alkaryl radicals such as tolyl and xylyl; alicyclic radicals such as cyclopentyl, cyclohexyl, 1-methylcyclohexyl, cyclo-octyl, and cyclohexylethyl; alkoxy radicals such as methoxy, ethoxy, propoxy, t-butoxy, —$OCH_2CH_2OCH_3$, —$O(CH_2CH_2)_2OCH_3$, and —$O(CH_2CH_2)_3OCH_3$; aryloxy radicals such as phenoxy; as well as silyl radicals such as —$Si(CH_3)_3$, —$Si(OCH_3)_3$, and —$Si(C_3H_7)_3$; amino radicals such as —$NH_2$, —$N(CH_3)_2$, —$NHCH_3$, and —$NH(C_2H_5)$; arylphosphine radicals such as —$P(C_6H_5)_2$; acyl radicals such as —$C(O)CH_3$, —$C(O)C_2H_5$, and —$C(O)C_6H_5$; carbonyloxy radicals such as —$C(O)OCH_3$; oxycarbonyl radicals such as —$O(CO)C_6H_5$; amido radicals such as —$CONH_2$, —$CON(CH_3)_2$, and —$NHC(O)CH_3$; sulfonyl radicals such as —$S(O)_2C_2H_5$; sulfinyl radicals such as —$S(O)CH_3$; sulfenyl radicals such as —$SCH_3$, —$SC_2H_5$, and —$SC_6H_5$; phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$. and —$P(O)(H)(C_6H_5)$.

Specific examples of organobisphosphites are Ligands A-S of WO 2008/115740.

The organomonophosphites that can be used in the practice of this invention include any organic compound comprising one phosphite group. A mixture of organomonophosphites can also be used. Representative organomonophosphites include those of formula (VIII).

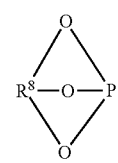
(VIII)

in which $R^8$ represents a substituted or unsubstituted trivalent hydrocarbon radical containing 4 to 40 carbon atoms or greater, such as trivalent acyclic and trivalent cyclic radicals, e.g., trivalent alkylene radicals such as those derived from 1,2,2-trimethylolpropane, or trivalent cycloalkylene radicals, such as those derived from 1,3,5-trihydroxycyclohexane.

Such organomonophosphites may be found described in greater detail, for example, in U.S. Pat. No. 4,567,306.

Representative diorganophosphites include those of formula (IX).

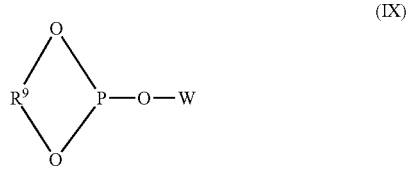

(IX)

in which $R^9$ represents a substituted or unsubstituted divalent hydrocarbon radical containing 4 to 40 carbon atoms or greater and W represents a substituted or unsubstituted monovalent hydrocarbon radical containing 1 to 18 carbon atoms.

Representative substituted and unsubstituted monovalent hydrocarbon radicals represented by W in formula IX include alkyl and aryl radicals, while representative substituted and unsubstituted divalent hydrocarbon radicals represented by $R^9$ include divalent acyclic radicals and divalent aromatic radicals. Illustrative divalent acyclic radicals include, for example, alkylene, alkylene-oxy-alkylene, alkylene-$NX^2$-alkylene, wherein $X^2$ is hydrogen or a substituted or unsubstituted hydrocarbon radical, alkylene-S-alkylene, and cycloalkylene radicals.

The more preferred divalent acyclic radicals are the divalent alkylene radicals, such as disclosed more fully, for example, in U.S. Pat. Nos. 3,415,906 and 4,567,302. Illustrative divalent aromatic radicals include, for example, arylene bisarylene, arylene-alkylene, arylene-alkylene-arylene, arylene-oxy-arylene, arylene-$NX^2$-arylene, wherein $X^2$ is as defined above, arylene-S-arylene, and arylene-S-alkylene. More preferably, $R^9$ is a divalent aromatic radical, such as disclosed more fully, for example, in U.S. Pat. Nos. 4,599,206 and 4,717,775.

Representative of a more preferred class of diorganomonophosphites are those of formula (X).

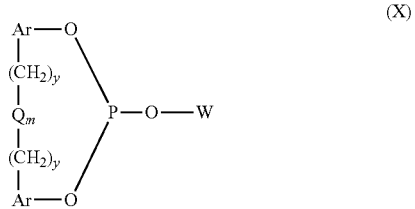

(X)

in which W is as defined above, each Ar is the same or different and represents a substituted or unsubstituted divalent aryl radical, each y is the same or different and is value of 0 or 1, Q represents a divalent bridging group selected from —$C(R^{10})_2$—, —O—, —S—, —$NR^{11}$—, —$Si(R^{12})_2$— and —CO, in which each $R^{10}$ is the same or different and represents hydrogen, alkyl radicals having from 1 to 12 carbon atoms, phenyl, tolyl, and anisyl, $R^{11}$ represents hydrogen or an alkyl radical of from 1 to 10 carbon atoms, preferably, methyl, each $R^{12}$ is the same or different and represents hydrogen or an alkyl radical having 1 to 10 carbon atoms, preferably, methyl, and m is a value of 0 or 1. Such diorganomonophosphites are described in greater detail, for example, in U.S. Pat. Nos. 4,599,206, 4,717,775 and 4,835,299.

Representative triorganomonophosphites include those of formula (XI).

(XI)

in which each $R^{13}$ is the same or different and is a substituted or unsubstituted monovalent hydrocarbon radical, for example, an alkyl, cycloalkyl, aryl, alkaryl, or aralkyl radical, which may contain from 1 to 24 carbon atoms. Illustrative triorganomonophosphites include, for example, trialkylphosphites, dialkylarylphosphites, alkyldiarylphosphites, and triarylphosphites, such as, triphenylphosphite, tris(2,6-triisopropyl)phosphite, tris(2,6-di-tert-butyl-4-methoxyphenyl) phosphite, as well as the more preferred tris(2,4-di-tert-butylphenyl) phosphite. The monovalent hydrocarbon radical moieties themselves may be functionalized with the proviso that the functional groups do not significantly interact with the transition metal or otherwise inhibit hydroformylation. Representative functional groups include alkyl or aryl radicals, ethers, nitriles, amides, esters, —$N(R^{11})_2$, —$Si(R^{12})_3$, phosphates, and the like, in which $R^{11}$ and $R^{12}$ are as previously defined. Such triorganomonophosphites are described in more detail in U.S. Pat. Nos. 3,527,809 and 5,277,532.

As a further option any organomonophosphite-monophosphate ligand or organomonophosphite-polyphosphate ligand may be employed as the organomonophosphite ligand in this invention. For example, any of the organopolyphosphite ligands, including preferred organobisphosphite ligands as previously described, may be subjected to oxidation such that all but one of the phosphorus (III) atoms is converted into phosphorus (V) atoms. The resulting oxidized ligand can comprise an organomonophosphite-polyphosphate or, preferably, an organomonophosphite-monophosphate, which suitably is employed in a 2/1 molar excess relative to the transition metal so as to provide for the organomonophosphite ligand component used in the practice of this invention. As here used "organomonophosphite ligand" and like terms include organomonophosphite-monophosphate ligand and organomonophosphite-polyphosphate ligand (as appropriate to the text in which the term is used) unless specifically noted otherwise.

As a further option any organomonophosphoramidite ligand can be used as, or in combination with, the organomonophosphite ligand used in the practice of this invention, and any organopolyphosphoramidite ligand can be used as, or in combination with, the organopolyphosphite ligand used in the practice of this invention. Organophosphoramidite ligands are known, and they are used in the same manner as organophosphite ligands. Representative organophosphoramidite ligands are of formulae (XII-XIV).

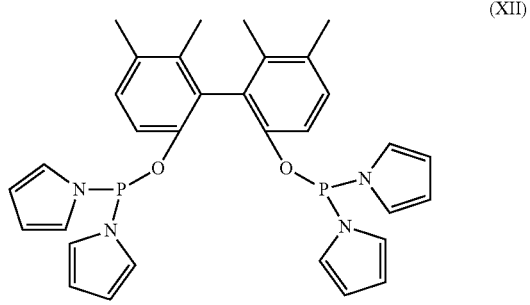

(XII)

(XIII)

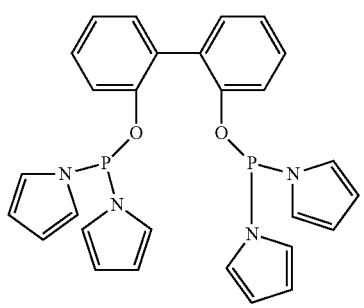

(XIV)

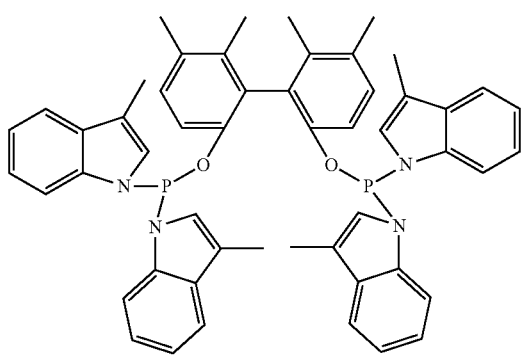

Organophosphoramidites are further described in, for example, U.S. Pat. No. 7,615,645. As here used "organomonophosphite ligand" and like terms include organomonophosphoramidite ligands unless specifically noted otherwise, and "organopolyphosphite ligand" and like terms include organopolyphosphoramidite ligands unless specifically noted otherwise.

The hydroformylation catalyst comprises a stabilized complex of (1) transition metal carbonyl hydride; (2) organobisphosphite ligand which is provided in the catalyst system at concentrations up to and including a 1:1 molar basis with respect to the transition metal component of the stabilized catalyst complex; and (3) monodentate phosphite ligand which is provided in excess molar quantity with respect to the rhodium metal component of the stabilized catalyst complex.

The catalyst can be prepared in situ in a hydroformylation reaction zone or, alternatively, it can be prepared ex-situ and subsequently introduced into the reaction zone with the appropriate hydroformylation reactants. In one embodiment the catalyst is prepared by admixing one mole of suitable transition metal source with 0.1 mole of organobisphosphite ligand and between about 5-100 moles of organomonophosphite ligand. In one embodiment the catalyst is prepared by admixing at a ratio of one mole of a suitable rhodium source to 5-100 moles of the monodentate phosphite ligand and after initiation of the hydroformylation reaction, the bisphosphite ligand (<1 mole) is added.

The catalytic species may comprise a complex catalyst mixture in its monomeric, dimeric or higher nuclearity forms which preferably are characterized by at least one organophosphorus-containing molecule complexed per one molecule of transition metal. For instance, the transition metal may be complexed with carbon monoxide and hydrogen in addition to either a monodentate phosphite ligand or a bisphosphite ligand.

The catalyst and its preparation are more fully described in U.S. Pat. Nos. 4,169,861, 5,741,945, 6,153,800 and 7,615,645, and WO 2008/115740.

The hydroformylation catalysts may be in homogeneous or heterogeneous form during the reaction and/or during the product separation. The amount of metal-ligand complex catalyst present in the reaction medium need only be that minimum amount necessary to catalyze the process. If the transition metal is rhodium, then concentrations in the range of 10 to 1000 parts per million (ppm), calculated as free rhodium, in the hydroformylation reaction medium is sufficient for most processes, while it is generally preferred to employ from about 10 to 500 ppm rhodium, and more preferably from 25 to 350 ppm rhodium.

In addition to the metal-ligand complex catalyst, free ligand (i.e., ligand that is not complexed with the metal) may also be present in the hydroformylation reaction medium. The free phosphite or phosphoramidite ligand, mono- or polydentate, is preferably, but not necessarily, the same as the phosphite or phosphoramidite ligand of the metal-phosphite or metal phosphoramidite ligand complex catalyst employed. The hydroformylation process of this invention may involve from 0.1 moles or less to 100 moles or higher, of free ligand per mole of metal in the hydroformylation reaction medium. Preferably the hydroformylation process is carried out in the presence of from 1 to 50 moles of ligand, and more preferably from 1.1 to 4 moles of ligand, per mole of metal present in the reaction medium; the amounts of ligand being the sum of both the amount of ligand that is bound (complexed) to the metal present and the amount of free (non-complexed) ligand present. Of course, if desired, make-up or additional ligand can be supplied to the reaction medium of the hydroformylation process at any time and in any suitable manner, e.g. to maintain a predetermined level of free ligand in the reaction medium.

As a general procedure, the catalyst system is first formed in a deoxygenated solvent medium in a hydroformylation reaction zone. Excess monodentate ligand can perform as the solvent medium. The first hydroformylation zone is pressured with hydrogen and carbon monoxide and heated to a selected reaction temperature. The olefinically unsaturated compound is then fed to the first hydroformylation zone, and the reaction is conducted until the desired conversion yield and efficiency have been attained at which time the product of the first reaction zone is transferred to the subsequent reaction zone(s) in which fresh and/or recycled reagents are added. The reaction in this subsequent reaction zone (or additional subsequent reaction zones) continues until the desired conversion yield and efficiency are attained at which time the product of the last reaction zone is recovered and purified. In a continuous system the catalyst is preferably recycled back to the first reaction zone.

The reaction conditions of the hydroformylation process can vary widely. For instance, the $H_2$:CO molar ratio of gaseous hydrogen to carbon monoxide advantageously can range from 1:10 to 100:1 or higher, the more preferred hydrogen to carbon monoxide molar ratio being from 1:10 to 10:1. Advantageously, the hydroformylation process can be conducted at a reaction temperature greater than −25° C., more preferably, greater than 50° C. The hydroformylation process advantageously can be conducted at a reaction temperature less than 200° C., preferably, less than 120° C. Advantageously, the total gas pressure comprising olefinic reactant, carbon monoxide, hydrogen, and any inert lights can range from 1 psia (6.9 kPa) to 10,000 psia (68.9 MPa). Preferably, the process be operated at a total gas pressure comprising olefinic reactant, carbon monoxide, and hydrogen of less than 2,000 psia (13,800 kPa), and more preferably, less than 500 psia (3450 kPa). Advantageously, the carbon monoxide partial pressure varies from 1 psia (6.9 kPa) to 1000 psia (6,900 kPa), and preferably from 3 psia (20.7 kPa) to 800 psia (5,516 kPa), and more preferably, from 15 psia (103.4 kPa) to 100 psia (689 kPa); while the hydrogen partial pressure varies preferably from 5 psia (34.5 kPa) to 500 psia (3,450 kPa), and more preferably from 10 psia (69.0 kPa) to 300 psia (2,070 kPa).

The feed flow rate of synthesis gas ($CO+H_2$) can vary widely over any operable flow rate sufficient to obtain the desired hydroformylation process. The syngas feed flow rate depends upon the specific form of catalyst, olefin feed flow rate, and other operating conditions. Likewise, the vent flow rate from the oxo reactor(s) can be any operable flow rate sufficient to obtain the desired hydroformylation process. Vent flow rate is dependent upon the scale of the reactor and the purity of the reactant and syngas feeds. Suitable syngas feed flow rates and vent flow rates are well known or easily calculated by those skilled in the art. In one embodiment the $H_2$ and CO partial pressures are controlled such that the reaction is conducted under conditions in which the hydroformylation rate is positive order for syngas ($H_2$ and CO) partial pressures for the monophosphite catalyst and negative order for the CO partial pressure for the bisphosphite catalysts (such as described in WO 2008/115740 A1).

Inert solvent can be employed as a hydroformylation reaction medium diluent. A variety of solvents can be used including ketones such as acetone, methyl ethyl ketone, methyl isobutyl ketone, acetophenone, and cyclohexanone; aromatics such as benzene, toluene and xylenes; halogenated aromatics including o-dichlorobenzene; ethers such as tetrahydrofuran, dimethoxyethane and dioxane; halogenated paraffins including methylene chloride; paraffinic hydrocarbons such as heptane; and the like. The preferred solvent is the aldehyde product and/or the oligomers of the aldehyde product, along with the reactive olefin or olefins.

In one embodiment the hydroformylation process is carried out in a multi-staged reactor such as described in U.S. Pat. No. 5,763,671. Such multi-staged reactors can be designed with internal, physical barriers that create more than one theoretical reactive stage or zone per vessel. The effect is like having a number of reactors inside a single continuous stirred tank reactor vessel. Multiple reactive stages within a single vessel are a cost effective way of using the reactor vessel volume. It significantly reduces the number of vessels that otherwise are required to achieve the same results. Obviously, however, if the goal is to have different partial pressures of a reactant in different stages of the process, then two or more reactors or vessels are employed. Reaction zones can be in parallel or series but most preferably are in series.

The hydroformylation process of this invention is typically conducted in a continuous manner. Such processes are well known in the art and may involve: (a) hydroformylating the olefinic starting material(s) with carbon monoxide and hydrogen in a liquid homogeneous reaction mixture comprising a solvent, the metal-phosphite ligand complex catalyst, free phosphite ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode in which a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass without recycling the unreacted olefinic starting material(s). Such types of recycle procedure are well known in the art and may involve the liquid recycling of the metal-phosphite complex catalyst fluid separated from the desired aldehyde reaction product(s), such as disclosed in U.S. Pat. No. 4,148,830 or a gas recycle procedure such as disclose in U.S. Pat. No. 4,247,486, as well as a combination of both a liquid and gas recycle procedure if desired. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

Without meaning to be bound by theory, the invention involves redistributing the portion of olefin conversion between the first and subsequent reaction zones in which the N/I ratio behavior of the different reaction zones are different. The bisphosphite catalyst reaction rate has a much higher dependence on the olefin partial pressure than the monophosphite catalyst. By shifting the portion of the total reaction from a reaction zone with a higher olefin partial pressure to one with a lower partial pressure, the bisphosphite catalyst reaction rate is decreased relative to the monophosphite catalyst. Since the bisphosphite catalyst typically exhibits high N:I relative to the monophosphite catalyst, the overall N:I is shifted lower quickly (and reversibly) without decomposing the bisphosphite ligand. This can be accomplished in one or more of three different means: (1) changing the temperature of one reaction zone, (2) changing the portion of the olefin reacting under low olefin partial pressure, or (3) changing the portion of the olefin reacted in the first reaction zone (by shorter or longer reaction time in the first reaction zone by means of olefin feed rate).

In one embodiment the first reactor runs at an N:I ratio of 3:1 to 10:1 while the second reactor runs at an N:I ratio of 1:2 to 2:1 (regardless of the obpl:metal molar ratio although it is usually greater than 0.8:1 if the olefin is propylene). This implies that the monodentate phosphite ligand is relatively more reactive at lower olefin partial pressure compared with that of bisphosphite ligand (the second reactor, having had most of the olefin reacted out up stream in the first reactor, has much lower olefin partial pressure). This means that a rapid decrease in the N:I ratio can be achieved by decreasing the temperature in the first reactor (reducing the reaction rate in the first reaction zone) and thus shifting unreacted olefin into the subsequent reaction zone(s). However, the magnitude of the change between the bisphosphite catalyst reactivity and the monodentate phosphite catalyst decreases as the olefin partial pressure increases, e.g., above 5 psi the olefin effect declines noticeably. In other words, as the olefin partial pressure decreases, the reactivity of the monodentate phosphite increases relative to the reactivity of the bisphosphite ligand. The monophosphite reaction rate is significantly less dependant on olefin partial pressure compared to the bisphosphite catalyst, which means that under these low olefin partial pressures, the monophosphite reaction rate is not reduced compared to the bisphosphite catalyst and thus the monophosphite catalyst is much more active than the bisphosphite catalyst (hence, lower N:I product is observed in the subsequent reaction zones where low olefin partial pressures are observed). The subsequent reactors can be run at the most efficient conversion conditions (e.g., higher temperature) to maintain acceptable overall olefin conversion efficiency if desired.

In one embodiment shifting some of the olefin feed directly into the second reactor, e.g., up to 20% without significant loss of olefin efficiency will also give a similar rapid decrease in N:I ratio. This is possible if the second reactor operates at lower olefin partial pressure than the first thus the amount of additional olefin added at this point is limited since more than 20% additional olefin will increase the olefin partial pressure closer to that of the first reaction zone (negating the effect) as well as giving a significant loss of olefin efficiency. The subsequent reactors can be run at the most efficient conversion conditions (e.g., higher temperature) to maintain acceptable overall olefin conversion efficiency if desired.

In one embodiment changing the reaction time in the first reaction zone will also enable rapid changes in N:I ratio. This can be accomplished by reducing system through-put (lower olefin feed rate) thus the olefin spends more time in the first reaction zone, reacting more of the olefin at higher N:I ratio leaving less olefin available to react in subsequent reaction zone(s) and the net overall N:I increases. Conversely, a faster feed rate "pushes" more unreacted olefin into subsequent reactors that give lower N:I ratio product and the net N:I ratio drops. Corresponding changes to syngas feed may be necessary to maintain proper stoichiometry but the portion of olefin converted in the first reaction zone will change thus impacting the overall product N:I ratio. The subsequent reactors can be run at the most efficient conditions (e.g., higher temperature) to maintain acceptable overall olefin conversion efficiency y if desired.

Specific Embodiments

General Procedure for Hydroformylation Process

The hydroformylation process is conducted in a glass pressure reactor operating in a continuous mode. The reactor consists of a three ounce pressure bottle partially submerged in an oil bath with a glass front for viewing. After purging the system with nitrogen, 20 ml of a freshly prepared rhodium catalyst precursor solution is charged to the reactor with a syringe. The catalyst precursor solution contains 100 ppm rhodium (introduced as rhodium dicarbonyl acetylacetonate), Ligand 1, and tetraglyme as solvent. After sealing the reactor, the system is purged with nitrogen and the oil bath is heated to furnish a reaction temperature of 80° C. The catalyst solution is activated with a feed of 1:1 CO and $H_2$ at a total operating pressure of 150 psig (1034 kPa) for 30 to 60 minutes. After the activation period, the reaction is initiated by the introduction of propylene. Flows of the individual gases are adjusted as desired, and nitrogen is added as necessary to maintain the desired total operating pressure of about 150 psig (1034 kPa). The flows of the feed gases ($H_2$, CO, propylene, $N_2$) are controlled individually with mass flow meters and the feed gases are dispersed in the catalyst precursor solution via fitted metal spargers. The partial pressures of $N_2$, $H_2$, CO, propylene, and aldehyde products are determined by analyzing the vent stream by GC analysis and Dalton's Law. The unreacted portion of the feed gases is stripped out with butyraldehydes products by the nitrogen flow to maintain substantially constant liquid level. The outlet gas is analyzed periodically by GC. If desired, samples of the reaction fluid may be withdrawn (via syringe) for $^{31}P$ NMR to determine the rate of decomposition of the ligands as a function of time under the reaction conditions. In practice, it is often observed that the system takes about one day to arrive at steady state conditions due to removing trace air from feed lines and reaching thermal equilibration of oil baths; so ligand decomposition studies are only initiated after steady state operations are achieved. This equipment also allows generating hydroformylation rates as a function of reaction temperature, CO and $H_2$ partial pressures, and Rh content.

The reaction system is initiated with rhodium/Ligand 1 to establish a preliminary steady state operation and then the isomer ratio is increased by adding a solution of Ligand 2.

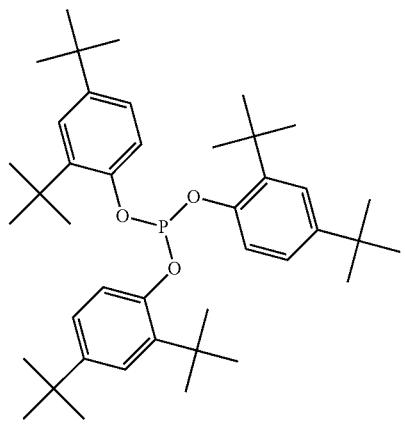

1

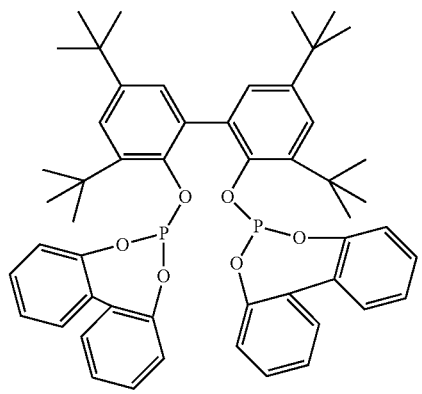

2

Ligand 1, a bulky organomonphosphite, and Ligand 2, an organopolyphosphite, have differing responses to olefin partial pressure and were combined with rhodium and evaluated as a variable selectivity catalyst system.

Charge to the glass reactor system a catalyst solution consisting of Rh(CO)$_2$(acac) (100 ppm Rh), Ligand 1 (10 equivalents/Rh) and tetraglyme (20 ml). Conditions are established as described below, maintaining a total operating pressure of 150 psia:

| Oil bath temp | ~80° C. |
|---|---|
| CO pressure | 50-57 psia |
| H$_2$ pressure | 50-57 psia |
| Propylene pressure | <1 psia |
| Nitrogen pressure | balance |

Once a consistent N:I is established, an aliquot of Ligand 2 was added via syringe (0.8 equivalents/Rh in toluene). The olefin partial pressure was adjusted and the resulting changes were determined. When necessary, sufficient time was allowed for the system to fully purge and reach a steady state (12-16 hours). The time line with the corresponding N:1 ratios can be seen below.

| Time (min) | Propylene Pressure (psi) | N:I Ratio |
|---|---|---|
| 0 | 0.31 | 1.0 |
| 162 | 0.44 | 1.1 |
| 318 | 0.50 | 1.2 |
| 484 | 0.50 | 1.2 |
| 640 | 0.46 | 1.2 |
| 797 | 0.85 | 1.2 |
| Added 0.8 eq of Ligand 2 | | |
| 46 | 2.30 | 1.8 |
| 77 | 2.27 | 2.8 |
| 108 | 2.16 | 3.7 |
| 149 | 2.38 | 5.4 |
| 182 | 2.08 | 6.1 |
| 213 | 1.98 | 5.9 |
| 244 | 1.88 | 5.5 |
| Increased Propylene | | |
| 36 | 18.28 | 6.2 |
| 58 | 28.00 | 8.7 |
| 89 | 20.11 | 9.1 |
| 120 | 19.34 | 9.1 |
| 151 | 20.15 | 9.4 |
| Reduced Propylene Purged System for 16 hrs | | |
| 0 | 1.72 | 3.3 |
| 156 | 1.34 | 3.0 |
| 291 | 1.06 | 2.9 |
| 426 | 0.96 | 2.8 |
| 566 | 0.93 | 2.7 |
| Increased Propylene | | |
| 0 | 31.27 | 6.4 |
| 31 | 23.50 | 7.2 |
| 62 | 20.03 | 7.0 |
| 93 | 20.68 | 6.5 |
| Reduced Propylene Purged System for 13 hrs | | |
| 0 | 2.09 | 3.4 |
| 156 | 2.29 | 2.8 |
| 312 | 1.67 | 2.8 |
| 624 | 1.64 | 2.6 |
| 937 | 1.90 | 2.5 |
| 1093 | 2.05 | 2.6 |

Because the N:I ratio is very sensitive to organopolyphosphite concentration, and because the organopolyphosphite decomposes slowly during the course of the experiment, one might expect for example, that the N:I resulting from a propylene partial pressure of about 2 psi at the beginning of the experiment will be somewhat higher than the N:I resulting from the same partial pressure at a later time. Nevertheless, the example clearly shows that for this rhodium/bulky organomonphosphite/organopolyphosphite catalyst system, the ratio of normal to isoaldehyde can be varied by simply increasing or decreasing the olefin partial pressure.

Although the invention has been described in considerable detail by the preceding specification, this detail is for the purpose of illustration and is not to be construed as a limitation upon the following appended claims.

What is claimed is:

1. A method of controlling a multiple-reaction zone, hydroformylation process for producing normal (N) and iso (I) aldehydes at a N:I ratio, the process comprising contacting an olefinically unsaturated compound with carbon monoxide, hydrogen and a catalyst comprising (A) a transition metal, (B) an organobisphosphite, and (C) an organomonophosphite ligand, the contacting conducted in first and subsequent reaction zones and at hydroformylation conditions comprising an olefinically unsaturated compound partial pressure in each zone, the method comprising changing the N:I ratio by one or more of the following:

(1) Changing the temperature in the first reaction zone;
   (2) Feeding up to 20% of the total olefin feed into a subsequent reaction zone;
   (3) Reducing the amount of olefin feed into a subsequent reaction zone;
   (4) Changing the olefin feed rate to the first reaction zone; and
   (5) decreasing the olefinically unsaturated compound partial pressure in the first reaction zone to decrease the N:I ratio or increasing the olefinically unsaturated compound partial pressure in the first reaction zone to increase the N:I ratio.

2. The method of claim 1 in which the olefinically unsaturated compound is an olefin having a total of from 3 to 10 carbon atoms.

3. The method of claim 1 in which the olefinically unsaturated compound is a $C_4$ raffinate I or $C_4$ raffinate II isomeric mixture comprising butene-1, butene-2, isobutylene, butane, and optionally, butadiene.

4. The method of claim 1 in which the olefinically unsaturated compound is propylene.

5. The method of claim 1 in which the syngas comprises carbon monoxide and hydrogen at a $H_2$:CO molar ratio of 10:1 to 1:10.

6. The method of claim 1 in which the catalyst comprises a stabilized complex of (A) rhodium carbonyl hydride; (B) bisphosphite ligand which is provided in the catalyst system at concentrations up to a 1:1 molar basis with respect to the rhodium metal component of the stabilized catalyst complex; and (C) monodentate phosphite ligand which is provided in excess molar quantity with respect to the rhodium metal component of the stabilized catalyst complex.

7. The method of claim 1 in which the catalyst is prepared by admixing at a ratio of one mole of a rhodium source to 5-100 moles of the monodentate phosphite ligand and after initiation of the hydroformylation reaction, adding 0.1 to less than one mole of the bisphosphite ligand.

8. The method of claim 7 in which the monodentate phosphite ligand is of the formula

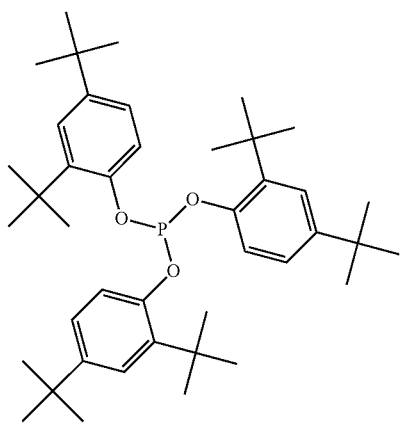 [SMILES: CC(C)(C)c1ccc(OP(Oc2ccc(C(C)(C)C)cc2C(C)(C)C)Oc2ccc(C(C)(C)C)cc2C(C)(C)C)c(C(C)(C)C)c1]

and the bisphosphite ligand is of the formula

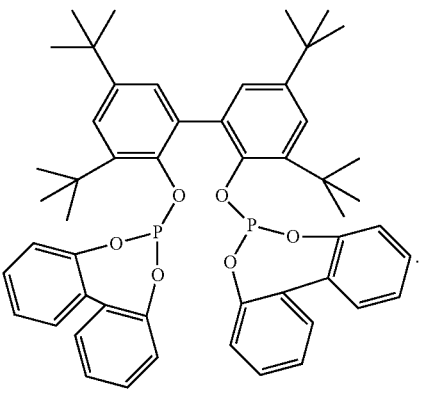 [SMILES: CC(C)(C)c1cc(-c2cc(C(C)(C)C)cc(C(C)(C)C)c2Op2oc3ccccc3c3ccccc3o2)c(Op2oc3ccccc3c3ccccc3o2)c(C(C)(C)C)c1]

9. The method of claim 1 in which the hydroformylation conditions include a reaction temperature greater than −25° C. and less than 200° C., and a total gas pressure comprising olefinic reactant, carbon monoxide, hydrogen, and any inert lights of 1 psia (6.8 kPa) to 10,000 psia (68.9 MPa).

10. The method of claim 1 in which the partial pressure of the olefinically unsaturated compound in the subsequent reactor is increased by decreasing the reaction that occurs in the first reaction zone.

11. The method of claim 1 in which the partial pressure of the olefinically unsaturated compound in the subsequent reaction zone is increased by decreasing the temperature in the first reaction zone.

12. The method of claim 1 in which the partial pressure of the olefinically unsaturated compound in the subsequent reaction zone is decreased by increasing the temperature in the first reaction zone.

13. The method of claim 1 in which the partial pressure of the olefinically unsaturated compound in the second reactor is increased by feeding a portion of the total olefin feed to a subsequent reaction zone.

14. The method of claim 1 in which the partial pressure of the olefinically unsaturated compound in a subsequent reactor is increased by increasing the olefin feed to the first reaction zone.

15. The method of claim 1 in which the changing the temperature in the first reaction zone comprising at least one of decreasing the temperature to decrease the N:I ratio and increasing the temperature to increase the N:I ratio.

16. The method of claim 1 in which the feeding up to 20% of the total olefin feed into a subsequent reaction zone decreases the N:I ratio.

17. The method of claim 1 in which the reducing the amount of olefin feed into a subsequent reaction zone increases the N:I ratio.

18. The method of claim 1 in which the changing the olefin feed rate to the first reaction zone comprises at least one of increasing the olefin feed rate to decrease the N:I ratio and decreasing the olefin feed rate to increase the N:I ratio.

* * * * *